(12) United States Patent
Redmond et al.

(10) Patent No.: US 7,151,099 B2
(45) Date of Patent: *Dec. 19, 2006

(54) USE OF TAUROLIDINE AND/OR TAURULTAM FOR TREATMENT OF ABDOMINAL CANCER AND/OR FOR THE PREVENTION OF METASTASES

(75) Inventors: H. Paul Redmond, Wilton (IE); Rolf W. Pfirrmann, Lucerne (CH)

(73) Assignee: Ed. Geistlich Soehne AG fuer Chemische Industrie, Wolhusen (CH)

( * ) Notice: Subject to any disclaimer, the term of this patent is extended or adjusted under 35 U.S.C. 154(b) by 772 days.

This patent is subject to a terminal disclaimer.

(21) Appl. No.: 09/971,774

(22) Filed: Oct. 9, 2001

(65) Prior Publication Data

US 2002/0091123 A1    Jul. 11, 2002

Related U.S. Application Data

(63) Continuation-in-part of application No. 09/493,797, filed on Jan. 28, 2000, now abandoned, which is a continuation of application No. PCT/GB98/02311, filed on Jul. 31, 1998.

(60) Provisional application No. 60/253,138, filed on Nov. 28, 2000, provisional application No. 60/246,100, filed on Nov. 7, 2000, provisional application No. 60/239,916, filed on Oct. 13, 2000.

(51) Int. Cl.
*A61K 31/727* (2006.01)
*A61K 31/54* (2006.01)

(52) U.S. Cl. .................. 514/222.5; 514/54; 514/55; 514/56; 514/62; 603/19; 603/28; 603/506

(58) Field of Classification Search ............ 514/54–56, 514/62, 222.5; 604/19, 28, 506
See application file for complete search history.

(56) References Cited

U.S. PATENT DOCUMENTS

| 5,077,281 | A |   | 12/1991 | Reinmuller | .................. 514/56 |
| 5,176,651 | A | * | 1/1993 | Allgood et al. | ............. 604/167 |
| 5,262,403 | A | * | 11/1993 | Nicolson et al. | ............. 514/56 |
| 5,725,553 | A |   | 3/1998 | Moenning | .................. 606/213 |
| 5,749,859 | A |   | 5/1998 | Powell | ........................ 604/164 |
| 5,763,421 | A |   | 6/1998 | Caretto et al. | ................. 514/56 |

| 6,479,481 | B1 |   | 11/2002 | Stendel et al. |

FOREIGN PATENT DOCUMENTS

| CA | 9530423 | 11/1995 |
| DE | 19606897 | 8/1997 |
| EP | 9200743 | 1/1992 |
| GB | 9518638 | 7/1995 |
| JP | 61000017 | 1/1986 |
| WO | WO 88/05301 | 7/1988 |

OTHER PUBLICATIONS

Physicians' Desk Reference, pp. 2034-3036, 1995.*
C.A. Jacobi et al., "Peritoneale instillation von Taurolidin und Heparin zur Verhinderung von intraperitonealem Tumorwaschstum und Trokarmetastasen bei laparoskopischen Operationen im Rattenmodell" Langenbecks Arch Chir, vol. 382, No. 4, suppl. 1, Jul. 25, 1997, pp. S31-S36.
Morgan McCourt et al., Taurolidine Inhibits Tumor Cell Growth In Vitro and In Vivo, *Annals of Surgical Oncology*, Jul. 17, 2000, 685-691, vol. 7, No. 9, Lippencott Williams & Wilkins, Ireland.
Embase abstract of J. Surg. Res. vol. 59, No. 6, pp. 764-771.
Treutner, K. et al "Prevention of postoperative adhesions by single intraperitoneal adhesion" J. Surg. Res. vol. 59, pp. 764-771, 1995.
Braumann, C., et al., "The Influence of Intraoperative Intravenous and Intraperitoneal Application of Taurolidine with Heparin on Subcutaneous and Intraperitoneal Tumor Growth in Laparoscopic Surgery in a Rat Model", *Department of Surgery, Humboldt-University of Berlin, Campus Chartié Mitte, Schumannstr.* 20-21, 10098 Berlin, Germany, Apr. 14th and 15th, 2000, 3 pages.
Jacobi, C.A., et al., "Influence of Different Gases and Intraperitoneal Instillation of Antiadherent or Cytotoxic Agents on Peritoneal Tumor Cell Growth and Implantation with Laparoscopic Surgery in a Rat Model", *Surg Endosc*, (1999) 13:1021-1025.
Jacobi, C.A., et al., "New Therapeutic Strategies to Avoid Intra-and Extraperitoneal Metastases during Laparoscopy: Results of a Tumor Model in the Rat", *Dig Surg*, 1999; 16:393-399.
Jacobi, C.A., et al., "Inhibition of Peritoneal Tumor Cell Growth and Implantation in Laparoscopic Surgery in a Rat Model", *The American Journal of Surgery*, (1997) vol. 174, pp. 359-363.
Monson, J.R.T., et al., "Preliminary Evidence that Taurolidine is Anti-neoplastic as well as Anti-endotoxin and Anti-microbial", *Br. J. Surg.*, A711, vol. 77, No. 6, Jun. 1990.
Monson, J.R.T., et al., "Taurolidine As An Anti-neoplastic Agent: A Previously Undiscovered role?", *Br. J. Surg.*, 1432, vol. 77, No. 12, Dec. 1990.

* cited by examiner

*Primary Examiner*—Leigh C. Maier
(74) *Attorney, Agent, or Firm*—Rothwell Figg Ernst & Manbeck

(57) ABSTRACT

Taurolidine and/or taurultam is administered during and after surgical removal of a cancerous tumor to treat abdominal cancer.

11 Claims, No Drawings

USE OF TAUROLIDINE AND/OR TAURULTAM FOR TREATMENT OF ABDOMINAL CANCER AND/OR FOR THE PREVENTION OF METASTASES

The present application is a continuation-in-part of U.S. Ser. No. 09/493,797, filed Jan. 28, 2000 now abandoned, which is a continuation of International Application No. PCT/GB98/02311, filed Jul. 31, 1998, and which claims foreign priority from GB 97 16219.2, filed Jul. 31, 1997. The present application also claims the benefit of U.S. Provisional Application Ser. No. 60/239,916, filed Oct. 13, 2000, U.S. Provisional Application Ser. No. 60/246,100, filed Nov. 7, 2000 and U.S. Provisional Application Ser. No. 60/253,138, filed Nov. 28, 2000.

BACKGROUND OF THE INVENTION

1. Field of the Invention

The present invention relates to cancer treatment.

2. Description of the Background Art

Prior art cancer treatments typically involve surgical removal of the cancerous tumor and subsequent treatment with anti-cancer drugs or radiation.

SUMMARY OF THE INVENTION

Taurolidine and/or taurultam is administered during and after surgery to treat abdominal cancer.

DETAILED DESCRIPTION OF THE INVENTION

The present invention relates to a method of treating abdominal cancer comprising performing a surgery on a patient's abdomen by forming a surgical opening in the patent's abdomen, and surgically removing a cancerous tumor from the patient's abdomen through the surgical opening. Prior to closing the surgical opening, taurolidine, taurultam or a mixture thereof is administered to the patient's abdomen so as to treat cancer in the patient's abdomen. After the surgical opening in the patient's abdomen is closed, additional taurolidine, taurultam or a mixture thereof is administered to the patient. In certain embodiments, taurolidine, taurultam or a mixture thereof also is administered to the patient prior to performing the surgery to remove the tumor. Exemplary abdominal cancers include, but are not limited to, colon cancer, rectal cancer, pancreatic cancer, stomach cancer and lung cancer. Taurolidine, taurultam and mixtures thereof have been found to have anti-angiogenic activity when administered pre-operatively, peri-operatively and post-operatively in conjunction with transabdominal oncology surgery. In accordance with one embodiment, the taurolidine and/or taurultam may be administered in combination with administration of 5-fluorouracil (5-FU), wherein the 5-FU is administered at a dosage within the range of about 0.1–1000 mg per dosage unit.

This invention also relates to a method for preventing metastases, in particular to a method for preventing metastatic growth of malignant tumors. More particularly it relates to a method for preventing metastatic growth following surgery, and especially minimally invasive abdominal surgery, such as endoscopic, e.g. laparoscopic surgery.

Malignant tumors within the body, and particularly the abdomen are frequently removed surgically. The exploration and excision of tumors by major invasive surgery has been used for many years, but, more recently, minimal invasive surgery has increasingly been used.

A wide range of indications of malignant tumors exist for which invasive surgery, such as laparotomy or laparoscopy, may used. These include, but are not restricted to, the following: oesophagus carcinoma (plaster cell carcinoma, adenocarcinoma) and cardiacarcinoma; malignant degenerative ulcus; carcinoma of the stomach, antrum or corpus, malign adenoma of island cells, re-section or total gastrecomy; carcinoma of the gall duct or distal choledochus; carcinoma of the pancreas head, papilla, corpus or cauda; carcinoma of the small or large intestinal tract, sarcoma; colon malignancy; adeno carcinoma, lymphoma, malign carcinoid, melanoma, fibrosarcoma; carcinoma of the rectum; ovarial carcinoma; mama carcinoma; and prostate carcinoma.

The use of minimal invasive surgery has brought with it a reduced mortality and a reduced post-operative infection rate. Classic open abdominal surgery, or laparotomy, for example, may require less operation time than minimal invasive surgery, but involves long post-operative convalescence and a greater risk of infection, e.g. sepsis. One reason why minimal invasive laparoscopies are on the increase is the drastically reduced amount of time that the patient needs to spend recuperating both in hospital and at home. Laparoscopy also has the advantage that there is a significant reduction in wound scars and in post-operative complications associated with wound healing.

A wide range of laparoscopic procedures are in general use, including laparoscopic cholecystectomy, laparoscopic fundoplicatio (anti-reflex surgery for gastro-oesophageal disease), laparoscopic treatment of para-oesophageal hernia, laparoscopic treatment of abdominal cysts (e.g. liver cysts removed by cystectomy), laparoscopic liver re-section, laparoscopic appendectomy, laparoscopic treatment of intestinal obstruction (e.g. incarcerated hernias, colon obstruction and massively dilated small bowel obstruction), laparoscopic colo-rectal surgery (e.g. ileosacral re-section, hemicolectomy, sigma-resection, rectum prolapse and rectum amputation), laparoscopic adhesiolysis, emergency laparoscopy (explorative diagnosis), differential diagnosis of appendicitis, acute abdomen, ileus, abdominal trauma, and oncological queries (e.g. to determine whether or not carcinoma is operable).

One aspect of minimally invasive laparoscopies which gives rise to concern, particularly when these are used to combat abdominal malignancies, is the extent to which metastatic growth has been observed. It is now recognised that manipulation of a malignancy can result in a disturbance and release of malignant cells which can then travel to other locations where, if they adhere and start growing, form metastases with predictably unfortunate results. This risk is lower during a classic open laparotomy, for example, so that the whole tumour is carefully excised and removed without transferring any cells to other parts of the abdomen. In a minimally invasive laparoscopy using a trocar, however, this may not be possible and disturbance of the tumour and its contact with adjacent tissues whilst being removed are inevitable. It has been found that "trocar metastases" are often a result of minimally invasive abdominal surgical procedures, e.g. laparoscopic surgery.

One reason for the frequent observation of metastases following laparoscopic intervention is believed to reside in the use of the trocar tubes or sleeves, the diameters of which may range from 5 to 20 mm. These can either result in damage to malignant tissues or may otherwise come into contact with cell-rich exudate which then drips from the trocar sleeve into the abdominal cavity thereby initiating metastases. To effect the removal of re-sected organs or pieces from the abdomen, a "rescue" bag is introduced via the trocar sleeve. This is particularly so when removing inflamed re-sections or neoplastic tissue in an attempt to prevent contamination of the abdominal cavity by re-sected neoplastic cells or cell threads of the primary tumour.

We have now found that the incidence of metastases following surgery, and in particular trocar metastases believed to be caused by laparoscopic operations, can be reduced if the area affected during the operation and any other internal tissue or organ with which any of the apparatus or tumour comes into contact is instilled with a solution containing taurultam, taurolidine or a mixture thereof.

In studies that have been carried out on animal models, a significant suppression in the growth or spread of tumours following instillation of taurultam or taurolidine has been observed.

Accordingly, viewed from one aspect, we provide the use of taurultam or taurolidine solutions to prevent or reduce metastatic growth. This is of particular application in preventing or reducing the incidence of metastatic growth following surgery, and particularly following the use of trocars during minimal invasive laparoscopic surgery, but has general application.

Viewed from a further aspect, we provide the use taurolidine and/or taurultam in the manufacture of a medicament for the prevention of metastases, in particular for the prevention or reduction of metastatic growth.

A preferred solution will contain from 0.5 to 3% by weight of taurolidine, or from 2 to 3% by weight taurultam, depending on the solubility of the compound. Solutions containing from 0.5 to 1.0% or 2.0% taurolidine are preferred.

The solutions will generally be made up in sterile pyrogen-free water and may also contain, for example, inorganic or other salts or other components to render them isotonic. Parenterally acceptable polyols may, for example, also be present since these have been observed to increase the overall intravenous tolerance of taurolidine. Suitable polyols include carbohydrates, e.g. hexoses such as glucose and fructose (or mixtures of these such as invert sugar), pentoses such as xylose or polysaccharides such as dextran or hydrolysed starch; glycerol and sugar alcohols such as sorbitol, mannitol or xylitol.

The concentration of the polyol can usefully be in the range 3–40% by weight. In the case of glucose, the concentration may be in the range 10–30% by weight, preferably 20%.

The solutions may also contain polyvinylpyrrolidone (PVP). This may be incorporated into the solutions at a concentration of, e.g. from 4 to 7% by weight. A solution containing 5% PVP is preferred. This assists in solubilising the active substance and contributes also to the oncotic pressure of the solution. The molecular weight of the PVP should not be greater than 30,000 and is preferably less than 10,000, for example between 7000 and 9000. Kollidone 17 as sold by BASF is relatively quickly resorbed and excreted renally.

The exact mode of action of taurolidine or taurultam in preventing metastatic growth under these circumstances is still not known. Without wishing to be bound by theoretical considerations, we believe that the taurolidine or taurultam is capable of altering the protein structure surface of the adhesion molecules (receptors) such as I-P-selectine and fibronectine. It is believed that over-expression of molecules such as these, and including also integrine, vitronectine and laminin, are the principal cause of metastatic development since they are believed to provide the malignant cells with the ability to migrate and adhere to other cell surfaces and endothelium, in particular to vascular endothels. The malignant cells then become sedentary, allowing themselves to grow and further develop (metastases). Once developed, such cells are able to reach every organ either through the haematogenic or lymphatic channels (formation of metastases).

It is believed that the taurolidine or taurultam modifies the surface structure of the malignant cell in such a way that over-expression of the adhesion molecules is reduced. As a result, adhesion of the malignant cells to other cell surfaces and endothelium, e.g. to endothels, is reduced or does not occur before the cell itself dies. The active agent is not believed to have any direct cytotoxic effect on the malignant cells. Taurolidine or taurultam is also believed to prevent high cytokine levels, e.g. IL-1$\beta$, in peritoneal fluid, which in turn prevents tumor cell proliferation and adhesions. The taurolidine or taurultam is thus being used essentially prophylactically.

The taurolidine or taurultam solution may be used simply by instillation, as an aerosol (a nebulised solution of taurolidine or taurultam) and/or by intravenous infusion. When being used in conjunction with a surgical procedure, it may be administered either prior to, during or after the surgical procedure being carried out. If used as an instillation to irrigate the surgically affected area, it will be administered intra-operatively or before closure of the surgical incision. In minimal invasive surgery, the solution can be passed through the trocar tubes or sleeves.

In general, in preparation for laparoscopy the abdominal wall is lifted. This may be achieved either by insufflation (pneumoperitoneum) or mechanically. Special instruments are required to raise the abdominal wall without causing damage to the intestinal loops. A Veres needle having an opening on one side through which a gas may enter the abdominal cavity is generally used for preparation of the pneumoperitoneum. Gases conventionally used for insufflation include $N_2O$, $CO_2$ and helium which may be introduced into the abdominal cavity at a rate of up to 1 liter/min. Depending on the patient's body size and tissue tension, between 3 and 5 liters of $CO_2$ gas may be required. For diagnostic laparoscopy under local anaesthetic, $N_2O$ is preferred since, unlike $CO_2$, this does not irritate the peritoneum. Whilst not wishing to be bound by theory, it is believed that this irritation could be one of the reasons for the more frequent appearance of metastases observed when using $CO_2$.

A metal suspension bar is conveniently used to lift the abdominal wall mechanically. Once inserted into the abdomen, special hooks are attached to the suspension bar and the abdomen is then raised using a chain and suspension scale.

According to the type of surgical procedure, for example in minimally invasive abdominal surgery, from 100–1000 ml, preferably from 100–250 ml, of a 2%, 1% or 0.5% taurolidine solution can be instilled at body temperature and allowed to remain in the abdominal cavity after the end of the operative procedure, and before extraction of the gas used in the pneumoperitoneum (which enlarges the abdominal cavity and with which the laparoscopy starts) and final removal of the trocar.

For the prophylaxis of post-operative complications, particularly trocar metastases, a 2% Taurolin, a 0.5% Taurolin-Ringer or a 2–3% taurultam solution may be used. Conveniently, the abdomen is rinsed with such a solution using a rinse-suction tube. A 5 or 10 liter rinse bag is filled with the desired rinse solution (isotonic saline or ringer solution) and hung at a height of approx. 2 m. 1–2 liters of rinse solution are then introduced through the rinse-suction tube. Following a short contact time (sufficient to ensure that the intestinal loops are completely covered by the rinse solution) the solution is then suctioned off. In cases of severe inflammation, the rinsing solution will appear opaque such that abdominal visibility using the optic and camera is poor. In such cases, this rinsing procedure must be repeated until the liquid in the abdomen is clear and translucent.

When the rinsing procedure is complete and the solution is clear, the rinse bag is then filled with 250 ml 2% Taurolin (pre-warmed to 37° C.) which is allowed to flow into the abdominal cavity. Finally, a drain is inserted before closure of the abdomen. In severe cases, e.g. severe peritonitis, it is possible to instill (and in some cases to leave) up to 1000 ml Taurolin 2% solution within the abdominal cavity. In place of a 2% Taurolin solution, 1–1.5 liters Taurolin-Ringer 0.5% solution or a 2–3% taurultam solution may be used.

In patients with malignant tumours it is particularly advantageous to additionally administer Taurolin 2% intravenously through a central catheter as a drop infusion, e.g. at a dosage of 4×250 ml per day). If necessary, the drop infusion may be continued for 2–3 days following surgery.

Alternatively, the 2% Taurolin solution may be instilled and suctioned off using a pressure-rinse apparatus. Another variation is to attach a pressure-cuff to the rinse bag whereby suction may be carried out using a suction-off apparatus. It is also possible to use an infusion pump as an alternative to instillation.

In a preferred embodiment of the invention, the taurolidine or taurultam solution will be used simultaneously with heparin. The use of heparin alone has not been found significantly to influence metastatic growth but the use of heparin in conjunction with taurolidine, administered either in combination or separately, has been found to give a significant, synergistic effect. The desired dosage of heparin depends on the result of the blood coagulation test. Thus, this will vary from patient to patient but can nevertheless be readily determined by those skilled in the art. An average dosage of heparin can be expected to be in the range of from 230 to 625 I.U. heparin-Na/kg bodyweight. In general, 5000 I.U. heparin-Na might be administered up to 2 hours prior to surgery.

For use in laparoscopic surgery, standard-heparin-sodium or standard-heparin-calcium may be added to the taurolidine solution immediately prior to application. Alternatively, low molecular weight heparin may be used. Typically, 200–500 ml 0.5–1.0% Taurolin in isotonic saline or Ringer-solution may be administered in combination with 1000–5000 I.U. heparin via a trocar tube.

The taurolidine-heparin solution may conveniently be applied under pressure, e.g. approx. 10–12 mm Hg, by means of a micro-pump. Administered in this way, the solution enters the abdominal cavity as an aerosol, resulting in a more widespread application of the solution to all exposed interabdominal (interior and lateral) surfaces during surgery. Administration of the solution as an aerosol also results in an increased efficacy during pneumoperitoneum with carbon dioxide.

In an alternative embodiment of the invention, the taurolidine or taurultam solution may be used simultaneously with hyaluronic acid, e.g. with a 0.1% hyaluronic acid sodium salts pharmaceutical grade solution, preferably having a molecular weight of $2.5 \times 10^6$ Da.

Test Procedure

To prevent intraperitoneal tumour growth and trocar metastases caused by laparoscopic operations, the effect of taurolidine and heparin were investigated on the growth of colon carcinoma cells (DHD/L12/TRb) in vitro, as well as in rat models. After incubation of the cells with heparin, taurolidine or both substances there followed the in vitro determination of the growth kinetics of the cells. A second experiment followed on rats (n=60) following intraperitoneal application of tumour cells and subsequently the development of a pneumoperitoneum for 30 mins. The rats were randomised into 4 groups:

I Tumour cells
II Tumour cells+heparin
III Tumour cells+taurolidine
IV Tumour cells+taurolidine+heparin Results Where the tumour growth in vitro was not affected by heparin, a significant suppression of growth was observed with taurolidine and taurolidine/heparin. In vivo, however, the intraperitoneal tumour weight compared to the control group (596±278 mg) was reduced both with the instillation of heparin (298±155 mg) as well as with taurolidine (149±247 mg). The combination of both substances caused a further average tumour weight reduction of (21.5±36 mg). The development of trocar metastases could be significantly suppressed using either taurolidine alone, or the combination of taurolidine and heparin.

The following non-limiting examples serve to further illustrate the invention.

Example 1

Laparoscopic Procedure

In a typical abdominal procedure, which should not be considered as limiting, a 0.5% taurolidine Ringer solution at body temperature is rinsed through the suction rinse tube under minimal pressure intra-operatively.

According to the extent of surgical invasion, from 100–250 ml 2% taurolidine is instilled at 37° C. and allowed to remain in the abdominal cavity on conclusion of the operative procedure.

Example 2

Laparoscopic Procedure

A typical abdominal procedure may be carried out in accordance with Example 1, except that the 2% taurolidine solution is replaced by a 500 ml 0.5% taurolidine Ringer solution used in combination with 2500 I.U. heparin. This solution is instilled into the abdominal cavity via drains which are then clamped for 2 hours.

Example 3

Laparotomy (Partial Pancreatectomy)

In a typical treatment of pancreas head carcinoma, the operation site is meticulously rinsed with approx. 500–1000 ml warm (37° C.) 0.5% Taurolin-Ringer solution. After 10 minutes contact time, the solution is suctioned off.

Every 20 minutes the operation site is moistened with 100–200 ml 2% Taurolin solution using a large calibrated curved syringe.

After 10–15 minutes contact time the solution is suctioned off. Before final closure of the abdominal wall, 250 ml Taurolin 2% solution* (with heparin added according to the blood coagulation results) is instilled.

* Alternatively, 2–3% taurultam may be used.

Example 4

Laparotomy (Radical Mastectomy)

In a typical treatment of mamma carcinoma (radical mastectomy), the operation site is rinsed intra-operatively every 20 minutes using 200 ml Taurolin 2% solution. If possible, a 10 minute contact time is permitted by lifting the surgical drapes thereby preventing the rinse solution from draining away too quickly.

The operation wound is then closed and drained.

Additionally, intraoperative per drop infusion of 250 ml 2% Taurolin solution is administered via a central catheter (dosage: 4×250 ml per 24 hours).

Example 5

Laparoscopic Procedure

In a typical abdominal procedure, a taurolidine solution is administered in the form of an aerosol. This may be achieved through the use of a micro-pump which is situated between a gas (e.g. $CO_2$) supply and the abdominal cavity in which surgery is to be performed. A tube is used to carry the aerosol into the trocar tube or sleeve. The taurolidine solution may be administered continuously as a spray during abdominal surgery, e.g. at a rate of 100 to 200 ml per hour.

Example 6

Cancer patients are selected who are undergoing major abdominal cancer surgery. Two groups are patients are studied. Group A receives 250 ml taurolidine 2% solution drop infusion for two hours, followed by two hour intervals, a total of four times for a total administration of 1 liter taurolidine 2% solution. The taurolidine solution is administered intravenously through a central line prior to surgery. Group B receives saline vehicle control according to the same schedule. Taurolidine 2% solution is administered for two further doses post-operatively at six hour intervals. Antibiotic prophylaxis cover is given as Augmentin 1.2 g at induction and a further two doses given post-operatively. The effects of taurolidine 2% solution administered intravenously to cancer patients, including colon, rectum, pancreas, stomach and lung cancer patients, on angiogenic growth factors, were as follows: Reduction in serum vascular endothelial growth factors (VEGF) from 500–600 pg/ml to 350–360 pg/ml, Reduction of serum transforming growth factor (TGF-$\beta$) from 2,300–2,350 pg/ml to 990–1,050 pg/ml six hours post-operatively and to 1,700 pg/ml 24 hours post-operatively. Taurolidine 2% solution administered intravenously also decreased serum soluble adhesion molecules following surgery in cancer patients, including sE-selectin, sP-selectin and sVCAM-1.

Example 7

The effect of Taurolidine was examined on the growth of a rat metastatic colorectal tumor cell line (DHD/K12/TRb) in vitro and in vivo.

In the in vitro experiments, DHD/K12/TRb cells were incubated with 5, 10, 15, 25 µg/ml of Taurolidine. Cells incubated in culture medium alone were used as controls. Cell proliferation, cell viability, cell death, and cell apoptosis were measured using commercially available techniques.

In the in vivo experiment, BD IX rats were randomized into 2 groups (n=10/group). Group A (control) underwent laparotomy, instillation of DHD/K12/TRb tumor cells intra-peritoneally followed by phosphate buffered saline (PBS). Group B received Taurolidine (100 mg/kg) instead of PBS. Animals were sacrificed after 24 days and tumor burden assessed by counting the number of tumor nodules in the peritoneal cavity.

Incubation of the tumor cells with Taurolidine resulted in a 4 fold decrease in proliferation rates (25±4% v 100±28% for controls) and a 4 fold increase in cell necrosis as demonstrated by the increase in LDH release (403±28% v 100±26% for controls), at a Taurolidine concentration of 25 µg/ml. A dose dependent decrease in cell viability also was observed. In the in vivo study, local Taurolidine administration resulted in significant decreases in tumor burden (3±1 nodules in Group B animals vs 649±101 nodules in Group A animals). Taurolidine thus inhibits the growth of a rat metastatic colorectal tumor cell line in vitro and in vivo and prevents or reduces peritoneal metastates.

Example 8

The human colon cell lines SW 480 (primary), SW 620 (metastatic) and W 707 (metastatic) were incubated with the following: culture medium (control), taurolidine at 5, 10, 25, 50 and 100 µg/ml doses, and 5-Fluorouracil (5-FU) at 5, 10, 25, 50 and 100 µM doses. Cell proliferation, apoptosis and cell cycle were assessed.

There was a significant decrease in tumor cell proliferation at 24 hours as shown in the table (results as % of control). There was no significant increase in taurolidine-induced apoptosis and taurolidine did not alter the phases of the cell cycle. There was an increase in LDH release (p=0.0011), which correlated with inhibited tumor proliferation. Taurolidine was also compared with 5-FU and was found to be superior in inhibiting cell proliferation (p=0.001) and augmented the effects of given doses of 5-FU (p=0.0001).

| PROLIFERATION | Control | T 5 µg/ml | T 10 µg/ml | T 25 µg/ml | T 50 µg/ml | T 100 µg/ml | |
|---|---|---|---|---|---|---|---|
| SW 480 | 100 | 100.10 ± 0.18 | 101.68 ± 2.17 | 87.93 ± 2.95* | 53.55 ± 3.84* | 14.62 ± 4.40* | p = .0001 |
| SW 620 | 100 | 89.42 ± 1.85 | 90.22 ± 1.55 | 58.10 ± 14.86* | 25.01 ± 8.87* | 7.8 ± 1.35* | p = .0001 |
| SW 707 | 100 | 97.33 ± 4.06 | 88.48 ± 9.39 | 62.37 ± 24.27 | 36.81 ± 15.36* | 6.02 ± 0.26* | p = .0009 |

ANOVA (* vs controls)

Taurolidine inhibits the proliferation of these three human colon cell lines at doses within the therapeutic range and proved to be more effective than the above doses of 5-FU and it also enhanced the effects of 5-FU. It would appear to act as a direct cytotoxic agent on the tumor cells.

The invention claimed is:

1. A method of treating abdominal cancer comprising performing a surgery on a patient's abdomen by forming a surgical opening in said patient's abdomen, surgically removing a cancerous tumor from the patient's abdomen through the surgical opening, and closing said surgical opening, the method including a step of administering taurolidine, taurultam or a mixture thereof to the patient's abdomen prior to said closing of said surgical opening and after said surgically removing said cancerous tumor, so as to treat cancer in the patient's abdomen, further including a step of additionally administering taurolidine, taurultam or a mixture thereof to said patient after said closing said surgical opening wherein, after closing said surgical opening, said taurolidine, taurultam or mixture thereof is administered to said patient by installation or intravenous infusion, further including the step of additionally administering taurolidine, taurultam or a mixture thereof to said patient prior to forming said surgical opening in said patient's abdomen.

2. A method of treating abdominal cancer comprising performing a surgery on a patient's abdomen by forming a surgical opening in said patient's abdomen, surgically removing a cancerous tumor from the patient's abdomen through the surgical opening, and closing said surgical opening, the method including a step of administering taurolidine, taurultam or a mixture thereof to the patient's abdomen prior to said closing of said surgical opening and after said surgically removing said cancerous tumor, so as to treat cancer in the patient's abdomen, further including a step of additionally administering taurolidine, taurultam or a mixture thereof to said patient after said closing said surgical opening; further including the step of additionally administering taurolidine, taurultam or a mixture thereof to said patient prior to forming said surgical opening in said patient's abdomen.

3. The method of claim 2, wherein performing said surgery on said patient includes introducing a trocar tube into said patient during laparoscopic tumor surgery so as to conduct laparoscopic tumor surgery so as to conduct laparoscopic tumor surgery utilizing said trocar tube.

4. The method of claim 3 wherein during said surgery, said administering said taurolidine, taurultam or mixture thereof to said patient's abdomen is conducted by passing a solution containing said taurolidine, taurultam or mixture thereof through said trocar tube so as to contact internal tissue of the patient with said solution.

5. The method of claim 4 further comprising the step of withdrawing said trocar from said patient prior to said closing said surgical opening and prior to said step of additionally administering said taurolidine, taurultam or mixture thereof to said patient after closing said surgical opening.

6. The method of claim 3 wherein said cancerous tumor is selected from the group consisting of oesophagus carcinoma, cardiacarcinoma, malignant degenerative ulcus, stomach carcinoma, antrum carcinoma, corpus carcinoma, align adenoma of island cells, gall duct carcinoma, distal choledochus carcinoma, pancreas head carcinoma, pancreas papilla carcinoma, pancreas corpus carcinoma, pancreas cauda carcinoma, small intestinal tract carcinoma, large intestinal tract carcinoma, sarcoma, colon malignancy, adeno carcinoma, lymphoma, malign carcinoid, melanoma, rectal carcinoma, ovarial carcinoma, mamma carcinoma, and prostate carcinoma.

7. The method of claim 4, wherein said taurolidine, taurultam or a mixture thereof is present in a solution containing from 0.5 to 3% by weight said taurolidine or from 2 to 3% by weight said taurultam, or a mixture thereof.

8. The method of claim 7 wherein said solution further contains heparin, a heparin derivative or hyaluronic acid.

9. The method of claim 2 wherein said cancerous tumor is selected from the group consisting of colon cancer, rectal cancer, pancreatic cancer, stomach cancer and lung cancer.

10. The method of claim 2 further comprising administering to said patient 5-fluorouracil (5-FU) at a dosage within a range of about 0.1–1,000 mg.

11. A method of treating abdominal cancer comprising performing a surgery on a patient's abdomen by forming a surgical opening in said patient's abdomen, surgically removing a cancerous tumor from the patient's abdomen through the surgical opening, and closing said surgical opening, the method including a step of administering taurolidine, taurultam or a mixture thereof to the patient's abdomen prior to said closing of said surgical opening and after said surgically removing said cancerous tumor, so as to treat cancer in the patient's abdomen, further including a step of additionally administering taurolidine, taurultam or a mixture thereof to said patient after said closing said surgical opening, wherein performing said surgery on said patient includes introducing a trocar tube into said patient during laparoscopic tumor surgery so as to conduct laparoscopic tumor surgery so as to conduct laparoscopic tumor surgery utilizing said trocar tube, wherein during said surgery, said administering said taurolidine, taurultam or mixture thereof to said patient's abdomen is conducted by passing a solution containing said taurolidine, taurultam or mixture thereof through said trocar tube so as to contact internal tissue of the patient with said solution, further comprising the step of additionally introducing said solution into said patient prior to said laparoscopic tumor surgery and prior to introducing said trocar tube into said patient.

* * * * *